US011666321B2

(12) United States Patent
Danielson

(10) Patent No.: US 11,666,321 B2
(45) Date of Patent: Jun. 6, 2023

(54) RETRACTABLE TETHER IN APICAL PAD

(71) Applicant: Tendyne Holdings, Inc., St. Paul, MN (US)

(72) Inventor: Amy Marie Danielson, White Bear Lake, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 345 days.

(21) Appl. No.: 17/130,767

(22) Filed: Dec. 22, 2020

(65) Prior Publication Data
US 2021/0186687 A1 Jun. 24, 2021

Related U.S. Application Data
(60) Provisional application No. 62/952,666, filed on Dec. 23, 2019.

(51) Int. Cl.
*A61F 2/24* (2006.01)
*A61B 17/04* (2006.01)
*A61B 17/00* (2006.01)

(52) U.S. Cl.
CPC ........ *A61B 17/0401* (2013.01); *A61F 2/2457* (2013.01); *A61F 2/2481* (2013.01); *A61B 2017/00601* (2013.01); *A61B 2017/0496* (2013.01); *A61F 2/2409* (2013.01); *A61F 2/2427* (2013.01); *A61F 2220/0008* (2013.01); *A61F 2250/0012* (2013.01)

(58) Field of Classification Search
CPC ...... A61B 17/0401; A61B 2017/00601; A61B 2017/0496; A61F 2/2457; A61F 2/2481; A61F 2220/0008; A61F 2250/0012
See application file for complete search history.

(56) References Cited

U.S. PATENT DOCUMENTS

2016/0143736 A1* 5/2016 Vidlund ............. A61B 17/0401
623/2.4
2016/0367368 A1 12/2016 Vidlund et al.

FOREIGN PATENT DOCUMENTS

WO 2019231653 A1 12/2019

OTHER PUBLICATIONS

Extended European Search Report for Application No. 20216127.9, dated Jun. 9, 2021, 7 pages.

* cited by examiner

*Primary Examiner* — Suba Ganesan
(74) *Attorney, Agent, or Firm* — Wei & Sleman LLP

(57) ABSTRACT

An epicardial anchor system comprising a tether attachment member defining a portion of a tether passageway configured to receive a portion of a tether extending from a heart valve, a base having a rim defining a void along a circumference of the rim, and a tether capture device adjacent the tether attachment member and hingedly attached to the epicardial anchor, the tether capture device including an opening configured to receive the portion of the tether therethrough and a slot configured to capture the portion of the tether extending through the opening, and an actuation mechanism configured to flip the tether capture device from an unactuated condition to an actuated condition, wherein in the unactuated condition, the tether capture device is spaced from the void defined by the rim, and in the actuated condition, a first portion of the tether capture device is positioned within the void defined by the rim.

7 Claims, 15 Drawing Sheets

RETRACTABLE TETHER IN APICAL PAD

CROSS-REFERENCE TO RELATED APPLICATIONS

The present application claims the benefit of the filing date of U.S. Provisional Patent Application No. 62/952,666 filed Dec. 23, 2019, the disclosure of which is hereby incorporated herein by reference.

BACKGROUND OF THE DISCLOSURE

The present disclosure relates to devices and methods for securing a tether of a prosthetic heart valve to an anchor device.

Various options are available to maintain a prosthetic heart valve in a desired position within a native heart valve annulus of a patient. For example, the position of a surgical prosthetic heart valve may be maintained by suturing the prosthetic heart valve into the patient's native heart valve annulus. Collapsible and expandable prosthetic heart valves, on the other hand, may be maintained in a desired position by exerting radial forces against the native heart valve annulus and/or surrounding tissue. It may additionally be beneficial to assist collapsible and expandable prosthetic heart valves in maintaining the desired position through the use of a tether that extends from the prosthetic heart valve to an anchor on an exterior portion of the patient's heart. However, during or after the surgery, the tension on the tether and the position of the prosthetic heart valve may need to be readjusted, for example, if the prosthetic heart valve deviates from its intended position, or if the tension on the tether changes for any reason.

Thus, it would be preferable for a tether and the corresponding anchor to allow for post-surgical modifications to adjust the tension of the tether, or otherwise to adjust the position of the prosthetic heart valve post-surgery.

BRIEF SUMMARY

One aspect of the disclosure provides for an epicardial anchor system comprising a tether attachment member defining a portion of a tether passageway configured to receive a portion of a tether extending from a prosthetic heart valve, a base having a rim defining a void along a circumference of the rim, and a tether capture device adjacent the tether attachment member and hingedly attached to the epicardial anchor, the tether capture device including an opening configured to receive the portion of the tether therethrough and a slot configured to capture the portion of the tether extending through the opening, and an actuation mechanism configured to flip the tether capture device from an unactuated condition to an actuated condition, wherein in the unactuated condition, the tether capture device is spaced from the void defined by the rim, and in the actuated condition, a first portion of the tether capture device is positioned within the void defined by the rim.

Another aspect of the disclosure provides for a method of using an epicardial anchor comprising receiving a portion of a tether of a prosthetic heart valve within an opening of a tether capture device of the epicardial anchor while the prosthetic heart valve is positioned within a patient's heart, actuating an actuation mechanism to flip the tether capture device so that a first portion of the tether capture device is received within a recess defined by a rim, the rim defined by a base of the epicardial anchor device, the recess interrupting a circumference of the rim, and capturing the portion of the tether in the recess upon actuation of the tether capture device.

Another aspect of the disclosure provides for an epicardial anchor system comprising a tether configured to extend from a prosthetic heart valve, a tether attachment member defining a portion of a tether passageway configured to receive a portion of the tether, a base having a rim defining a void along a circumference of the rim, and a tether capture device adjacent the tether attachment member and hingedly attached to the epicardial anchor, the tether capture device including an opening configured to receive the portion of the tether therethrough and a slot configured to capture the portion of the tether extending through the opening, and an actuation mechanism configured to flip the tether capture device from an unactuated condition to an actuated condition, wherein in the unactuated condition, the tether capture device is spaced from the void defined by the rim, and in the actuated condition, a first portion of the tether capture device is positioned within the void defined by the rim.

BRIEF DESCRIPTION OF THE DRAWINGS

These and other features, aspects, and advantages of the present disclosure will become better understood with regard to the following description, and accompanying drawings.

DETAILED DESCRIPTION

Figure 1:
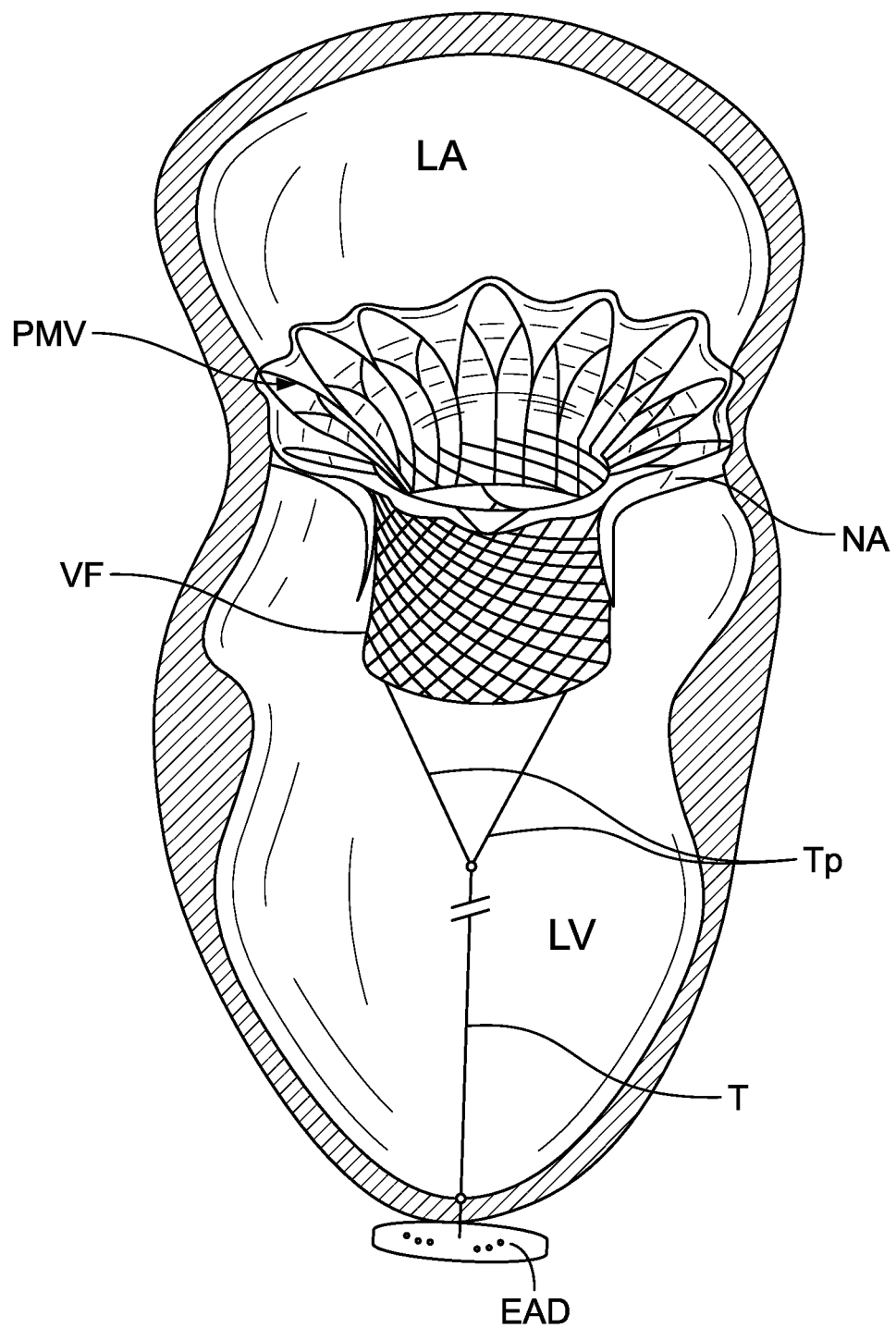
FIG. 1 depicts a cross-sectional illustration of a portion of a heart with a prosthetic mitral valve implanted therein and an epicardial anchor device anchoring the mitral valve in position.

Some devices for anchoring a medical device, such as a collapsible and expandable prosthetic heart valve, can include securing one or more tethers extending from the medical device to an anchor positioned on the heart, such as along an exterior portion of the ventricular wall. In one exemplary valve replacement procedure, the prosthetic heart valve may be delivered to a native valve annulus while in a collapsed state, and then allowed to expand to at least partially secure the prosthetic heart valve within the native valve annulus. If the prosthetic heart valve is for use in replacing a native mitral valve, a flared inflow end of the prosthetic heart valve may help prevent migration of the prosthetic heart valve into the left ventricle, while a tether attached to the prosthetic heart valve may assist in preventing migration of the prosthetic heart valve into the left atrium. During implantation, while the prosthetic heart valve is positioned within the valve annulus, a first end of the tether may be coupled to the prosthetic heart valve, and a second end of the tether may exit the heart, for example via a puncture in the left ventricular apex. While the second end of the tether is positioned outside the heart, an anchor may be slid over the tether until the anchor sits along the exterior portion of the ventricular wall such that an excess portion of the tether extends past the anchor outside the heart. The tether may then be tensioned until the prosthetic heart valve is at a desired tension and position within the patient's heart valve annulus. Once that desired tension is reached, the tether may be fixed to the anchor and the excess portion of the tether may be cut off and removed, thereby preventing excess length of the tether from freely floating within the patient's body and potentially interfering with the patient's surrounding anatomy.

However, after removal of the excess portion of the tether, there may be a desire to re-tension the tether. For example, such additional tensioning may be desirable if the prosthetic heart valve is not implanted in a desired position during surgery, or if the position shifts after surgery. Alternatively, tension readjustment may be desired after the surgery is complete and an interval of time has lapsed. In such an instance, the prosthetic heart valve may have been repositioned through wear or unintentional position shifts, or the native heart anatomy may have adjusted. For example, the tension on the tether may cause the ventricular wall to change shape, which in turn may reduce the tension of the tether. This biological adaption by the patient's heart can compound the need for an easily and quickly accessible means of adjusting the tether's tension as there is typically only a certain window of time (e.g., a few weeks, months, or the like) after implantation to perform such an adjustment, prior to tissue in-growth occurring in enough quantity to make further adjustment difficult or impossible. However, such an adjustment may be difficult or impossible if the excess portion of the tether has been cut off during surgery, as tensioning tools may require a certain length of tether extending from the anchor in order to properly grasp and apply a tensioning force. Thus, it may be beneficial to avoid cutting excess tether length to allow the excess tether portion to be accessed and retrieved, while simultaneously avoiding the excess tether length freely drifting within the patient.

FIG. 1 is a cross-sectional illustration of the left ventricle LV and left atrium LA of a heart having a transcatheter prosthetic mitral valve PMV deployed therein and an epicardial anchor device EAD as described herein securing the prosthetic mitral valve in place. FIG. 1 illustrates the prosthetic mitral valve PMV seated into the native annulus NA of the valve and held there using a valve frame VF of the prosthetic mitral valve, the radial tension from the native leaflets, and a ventricular tether T secured with attachment portions Tp to the prosthetic mitral valve and to the epicardial anchor EAD. An atrial flare portion (not separately labeled) of the valve frame VF may be positioned in the left atrium LA of the heart to prevent migration of the prosthetic mitral valve PMV into the left ventricle LV. Various embodiments of an epicardial anchor device are described in more detail below with reference to specific embodiments.

Figure 2:
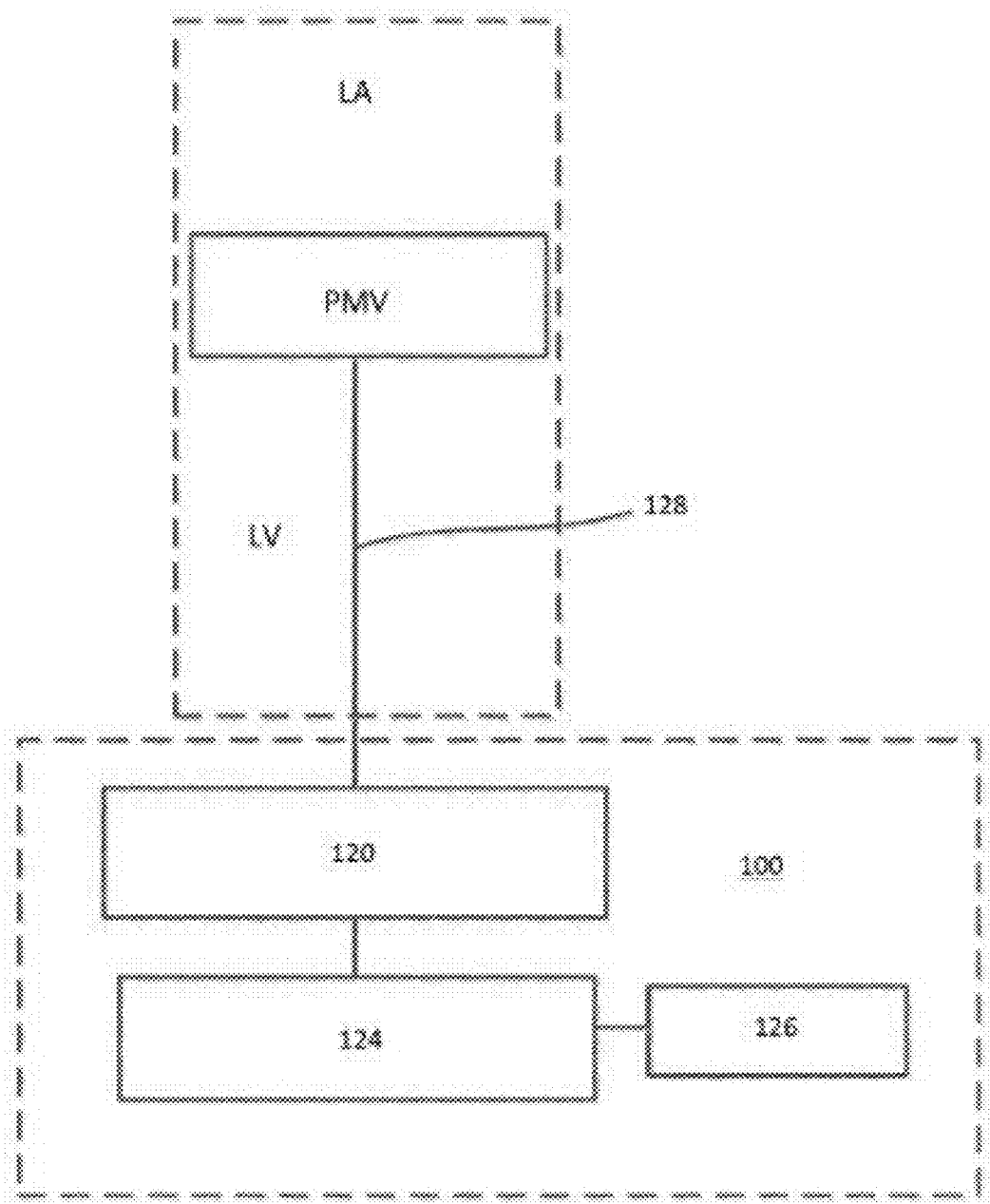
FIG. 2 depicts a schematic illustration of an epicardial anchor device, according to an embodiment of the present disclosure.
Figure 3:
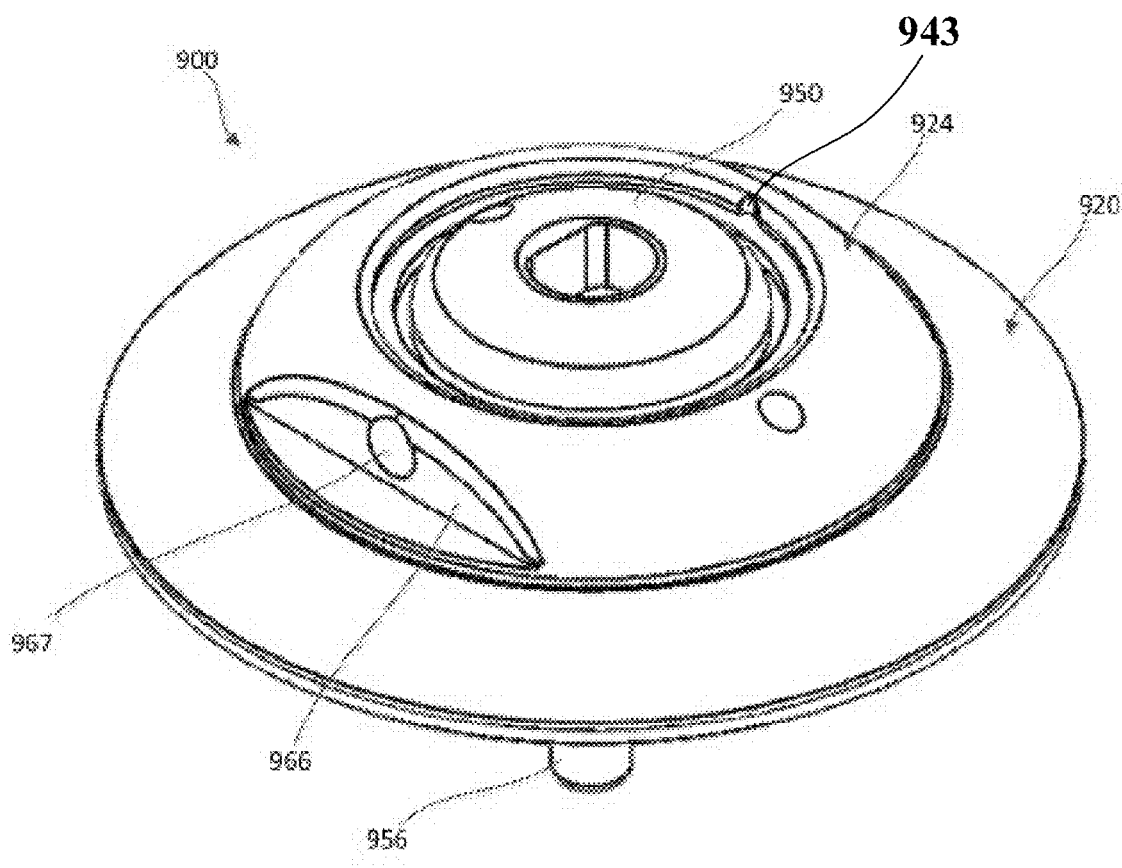
FIG. 3 depicts a perspective view of an epicardial anchor, according to an embodiment of the present disclosure.
Figure 4:
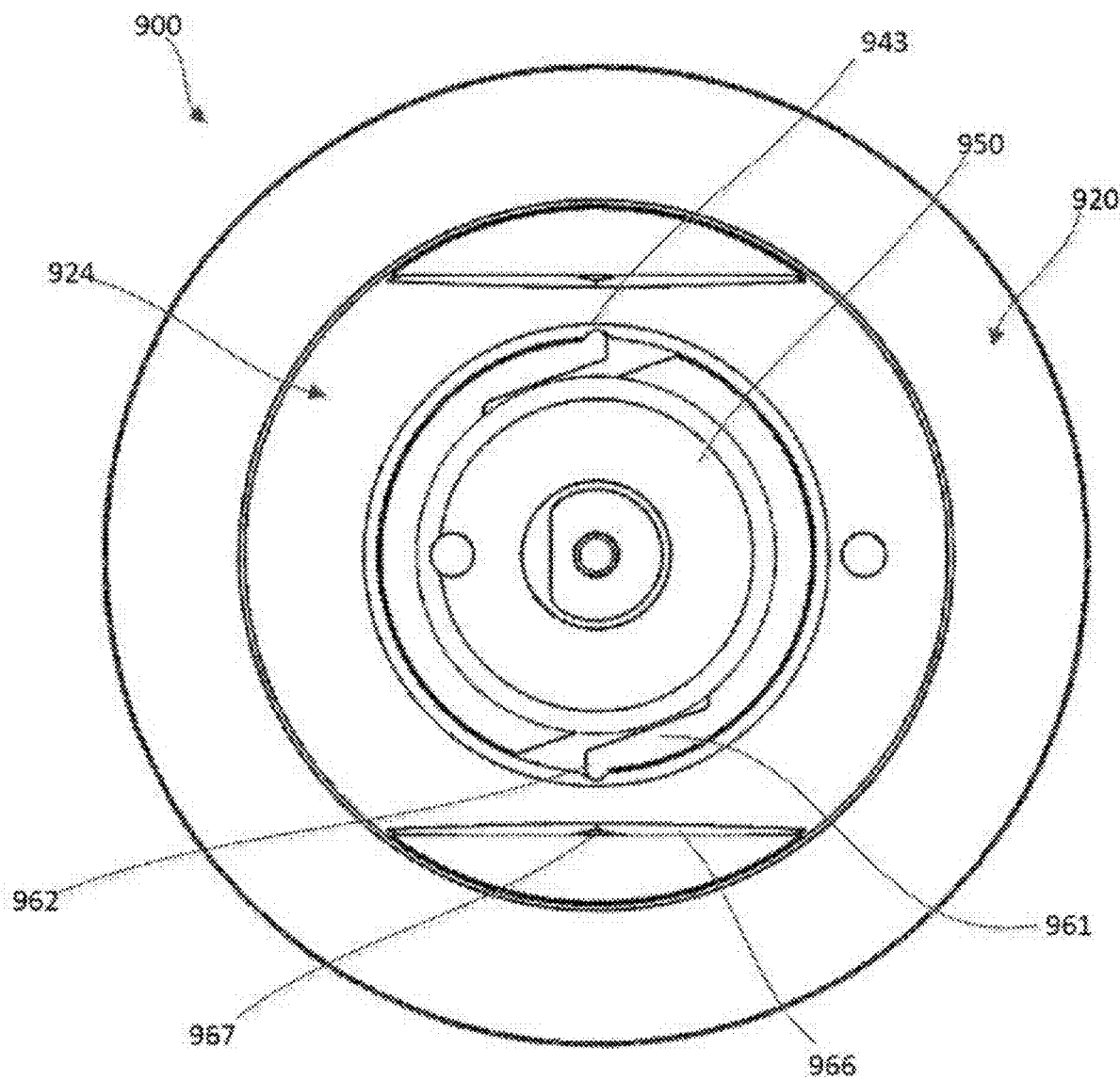
FIG. 4 depicts a top view of the epicardial anchor of FIG. 3.

FIG. 2 is a schematic illustration of an epicardial anchor device 100 (also referred to herein as "anchor," "anchor device," or "epicardial anchor") according to an embodiment of the disclosure. The anchor device 100 can be used to anchor or secure a prosthetic mitral valve PMV deployed between the left atrium LA and left ventricle LV of a heart. The anchor device 100 can be used, for example, to anchor or secure the prosthetic mitral valve PMV via a tether 128 as described above with respect to FIG. 1. The anchor device 100 can also seal a puncture formed in the ventricular wall (not shown in FIG. 2) of the heart during implantation of the prosthetic mitral valve PMV. The anchor device 100 can also be used in other applications to anchor a medical device (such as any prosthetic atrioventricular valve, including the tricuspid valve, or other heart valve) and/or to seal an opening such as a puncture.

The anchor device 100 can include a pad (or pad assembly) 120, a tether attachment member 124 and a locking pin 126. In some embodiments, the anchor device 100 can include a sleeve gasket (not shown in FIG. 2). The pad 120 can contact the epicardial surface of the heart and can be constructed of any suitable biocompatible surgical material. The pad 120 can be used to assist the sealing of a surgical puncture formed when implanting a prosthetic mitral valve. In some embodiments, the pad 120 can include a slot that extends radially to an edge of the pad such that the pad can be attached to, or disposed about, the tether 128 by sliding the pad onto the tether via the slot.

In some embodiments, the pad 120 can be made with a double velour material to promote ingrowth of the pad into the puncture site area. For example, pad or felt pledgets can be made of a felted polyester and may be cut to any suitable size or shape, such as those available from Bard® as PTFE Felt Pledgets having a nominal thickness of 2.87 mm. In some embodiments, the pad 120 can be larger in diameter than the tether attachment member 124. The pad 120 can have a circular or disk shape, or other suitable shapes.

The tether attachment member 124 can provide the anchoring and mounting platform to which one or more tethers 128 can be coupled (e.g., tied or pinned). The tether attachment member 124 can include a base member (not shown) that defines at least a portion of a tether passageway (not shown) through which the tether 128 can be received and pass through the tether attachment member, and a locking pin channel (not shown) through which the locking pin 126 can be received. The locking pin channel can be in fluid communication with the tether passageway such that when the locking pin 126 is disposed in the locking pin channel, the locking pin can contact or pierce the tether 128 as the tether passes through the tether passageway as described in more detail below with reference to specific embodiments.

The locking pin 126 can be used to hold the tether 128 in place after the anchor device 100 has been tightened against the ventricular wall and the tether has been pulled to a desired tension. For example, the tether 128 can extend through a hole in the pad 120, through a hole in a sleeve gasket (if the anchor device includes a sleeve gasket), and through the tether passageway of the tether attachment member 124. The locking pin 126 can be inserted or moved within the locking pin channel such that it pierces or otherwise engages the tether 128 as the tether extends through the tether passageway of the tether attachment member 124. Thus, the locking pin 126 can intersect the tether 128 and secure the tether to the tether attachment member 124.

The tether attachment member 124 can be formed with one or more of a variety of suitable biocompatible materials. For example, in some embodiments, the tether attachment member 124 can be made of polyethylene, or other hard or semi-hard polymer, and can be covered with a polyester velour to promote ingrowth. In other embodiments, the tether attachment member 124 can be made of metal, such as, for example, Nitinol®, or ceramic materials. The tether attachment member 124 can be various sizes and/or shapes. For example, the tether attachment member 124 can be substantially disk shaped.

In some embodiments, the tether attachment member 124 can include a hub that is movably coupled to the base member of a tether attachment member. The hub can define a channel that can receive a portion of the locking pin (or locking pin assembly) 126 such that as the hub is rotated, the hub acts as a cam to move the locking pin 126 linearly within the locking pin channel. In this manner, the locking pin 126 is moved from a first position in which the locking pin is spaced from the tether passageway to a second position in which the locking pin intersects the tether passageway and engages or pierces a portion of the tether.

In use, after a prosthetic mitral valve PMV has been placed within a heart, the tether extending from the prosthetic mitral valve can be inserted into the tether passageway of the anchor device 100 and the tension on the tether attachment member 124 can be adjusted to a desired tension. Alternatively, in some cases, the tether extending from the prosthetic mitral valve PMV can be coupled to the anchor device 100 prior to the prosthetic mitral valve being placed within the heart. The anchor device 100 (e.g., some portion of the anchor device such as the tether attachment member 124, or a lever arm, or hub depending on the particular embodiment) can be actuated such that the locking pin 126 intersects the tether passageway and engages a portion of the tether 128 disposed within the tether passageway, securing the tether to the tether attachment member. In some embodiments, prior to inserting the tether 128 into the tether passageway, the anchor device 100 can be actuated to configure the anchor device to receive the tether. For example, if the tether attachment member 124 includes a lever arm movably coupled to the base member, the lever arm may need to be moved to an open position to allow the tether to be inserted into the tether passageway.

FIGS. 3-11 depict an exemplary anchor device 900 capable of being used in conjunction with prosthetic mitral and tricuspid valves, including those disclosed in U.S. Patent App. Pub. No. 2016/0143736, the disclosure of which is hereby incorporated by reference herein. The epicardial anchor device 900 includes a tether attachment member 924, a pad assembly 920, a tube member 955 and a tube cover member 956. The tether attachment member 924 includes a base member 940, a hub 950, a retaining ring 952, a locking pin assembly 926, and a pin member 953. The locking pin assembly 926 includes a driver portion 946 and a piercing portion 949. The base member 940 defines a circumferential pad channel 942, a retaining channel 951 and a locking pin channel 934. The pad channel 942 can be used to couple the pad assembly 920 to the tether attachment member 924. The retaining channel 951 can receive an outer edge of the retaining ring 952, which is used to retain the hub 950 to the base member 940. The base member 940 also defines cutouts or detents 943, as shown for example, in FIGS. 3, 6, and 11.

The tube member 955 is coupled to the base member 940, and the base member, the hub 950 and the tube member collectively define a tether passageway 935 through which a tether (not shown) can be received. The tube cover member 956 can be formed with a fabric material, such as for example, Dacron®. The tether channel 935 intersects the locking pin channel 934 and is in fluid communication therewith. A portion of a top pad portion 958 is received within the channel 942 of the base member 940 as shown, for example, in FIGS. 6-8.

Figure 5:
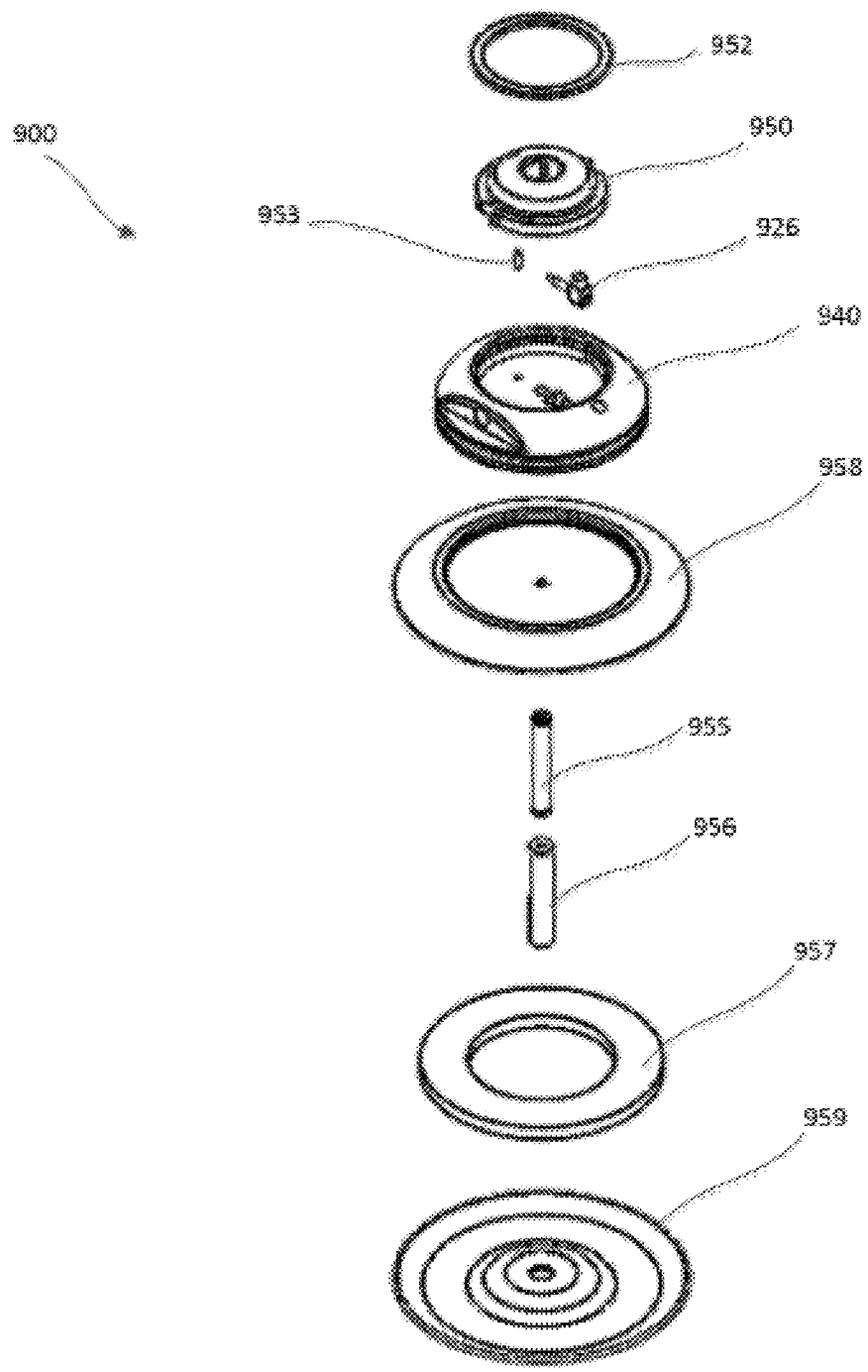
FIG. 5 depicts an exploded view of the epicardial anchor of FIG. 3.
Figure 6:
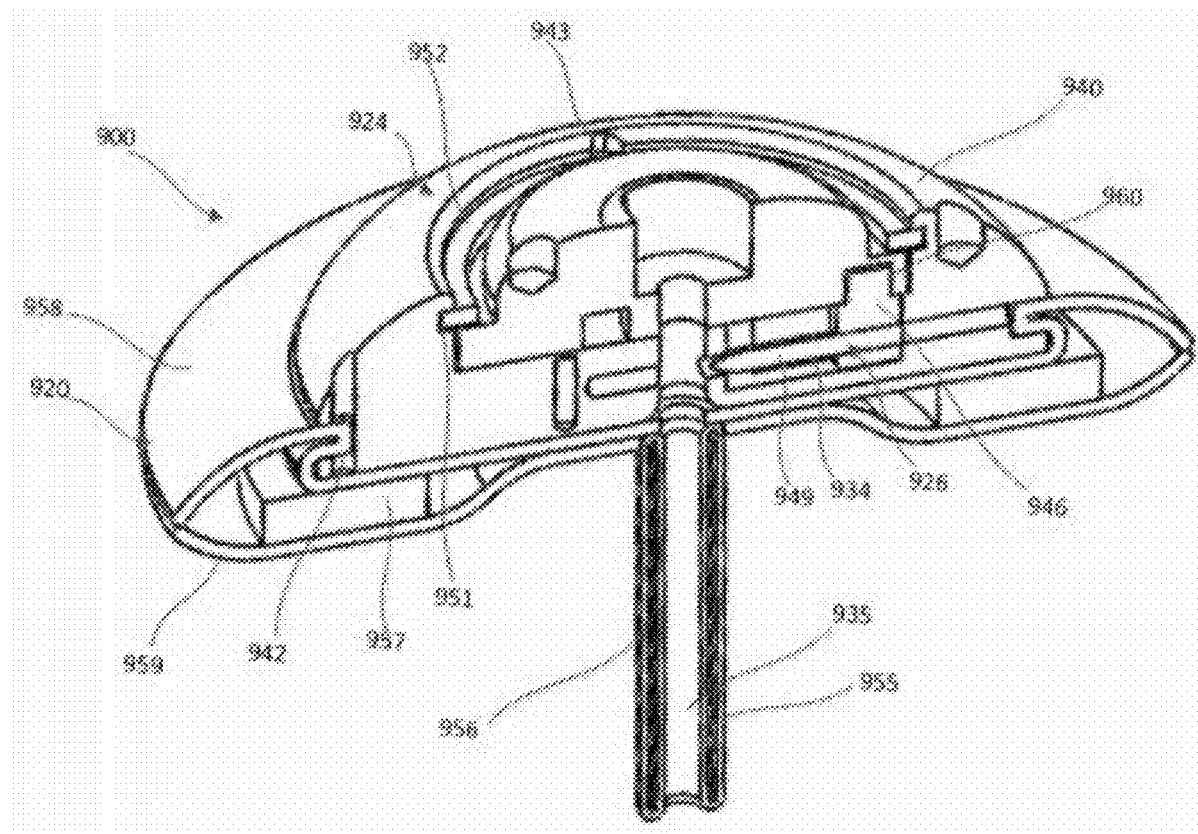
FIG. 6 depicts a perspective cross-sectional view of the epicardial anchor of FIG. 3.
Figure 7:
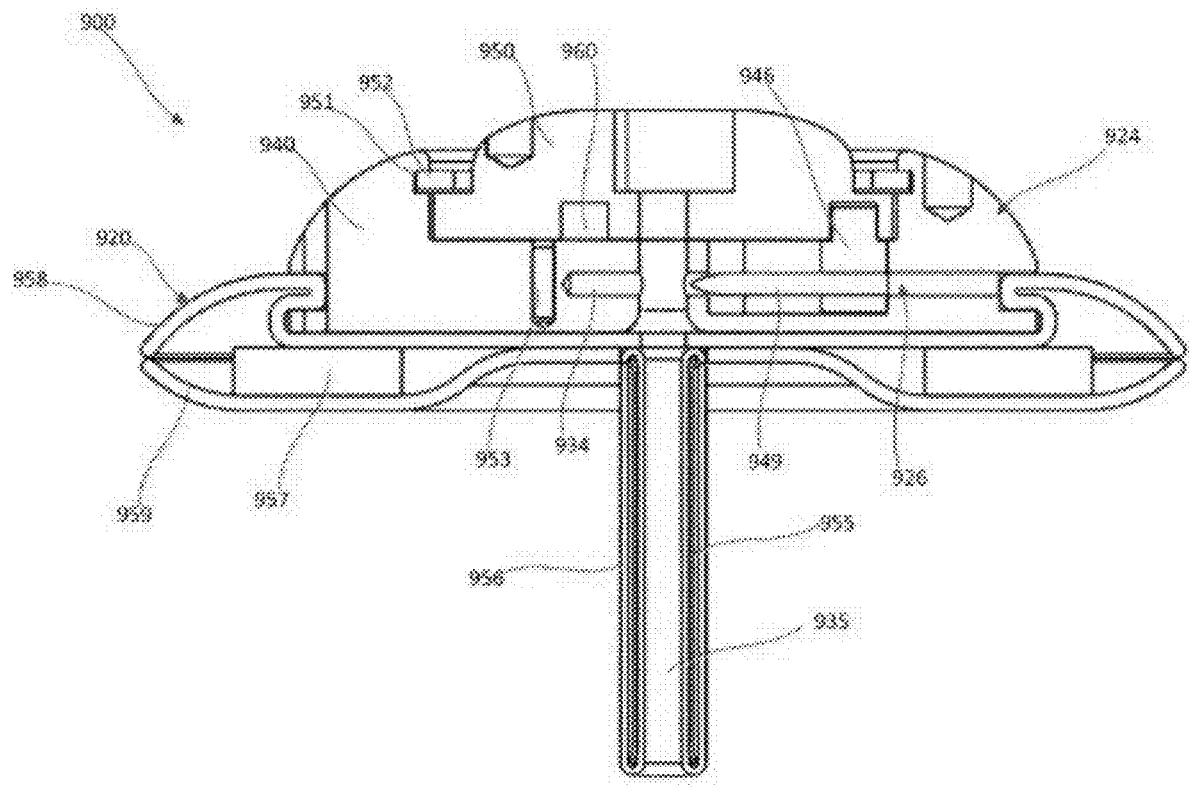
FIG. 7 depicts a front cross-sectional view of the epicardial anchor of FIG. 3.
Figure 8:
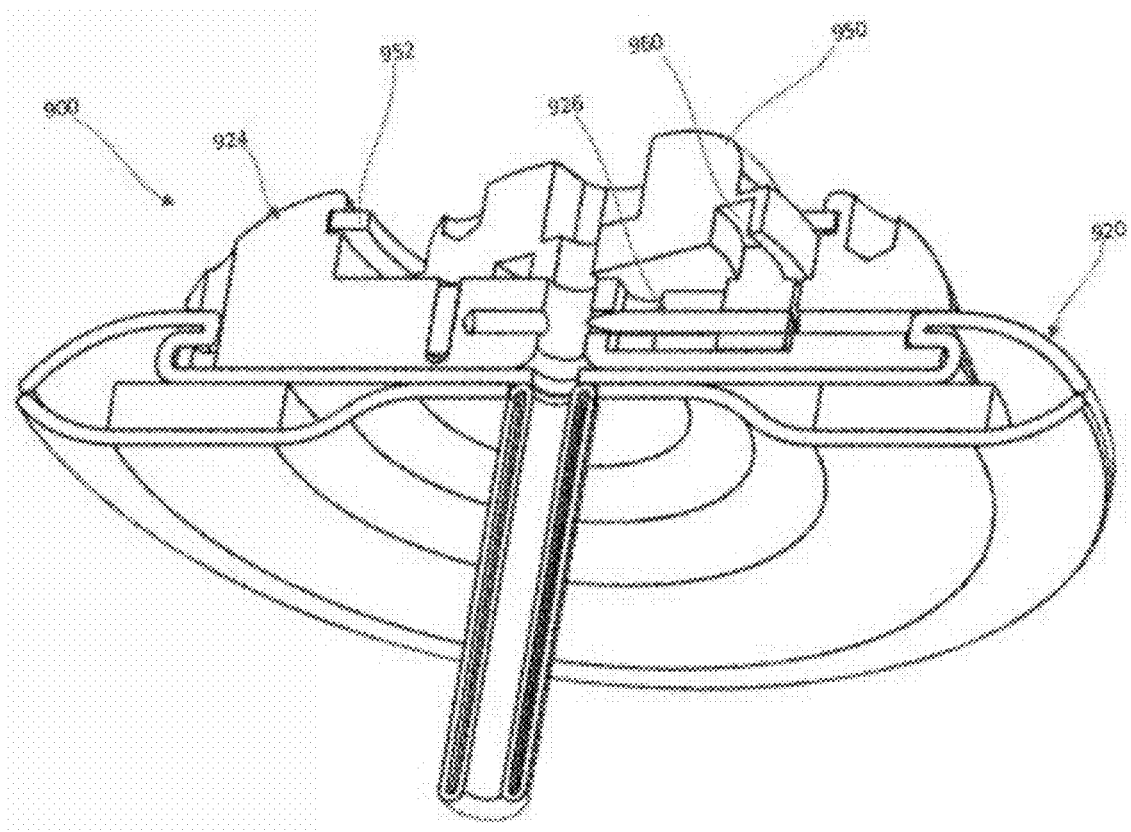
FIG. 8 depicts a perspective cross-sectional view of the epicardial anchor of FIG. 3.
Figure 9:
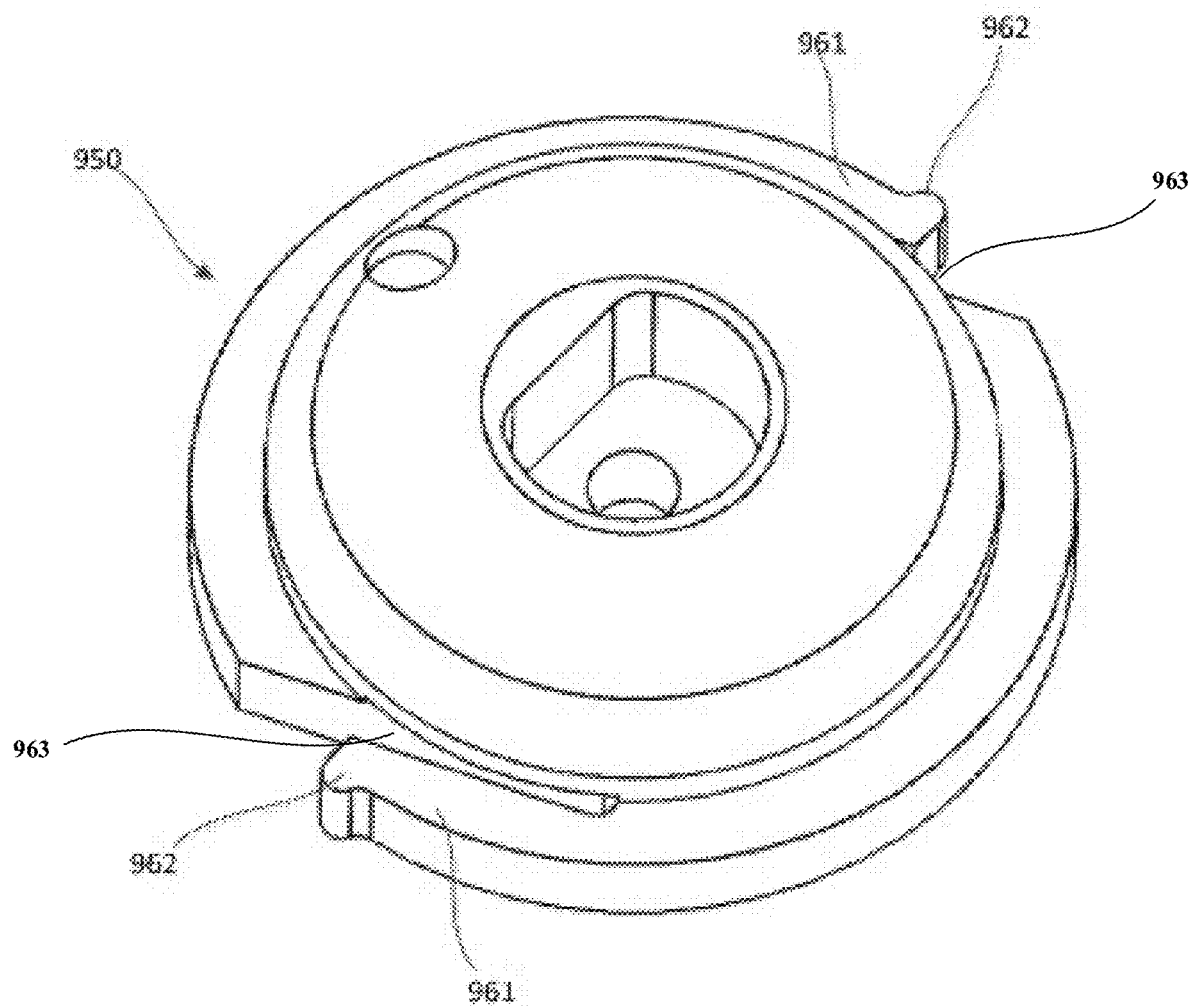
FIG. 9 depicts a top perspective view of a hub of the epicardial anchor of FIG. 3.
Figure 10:
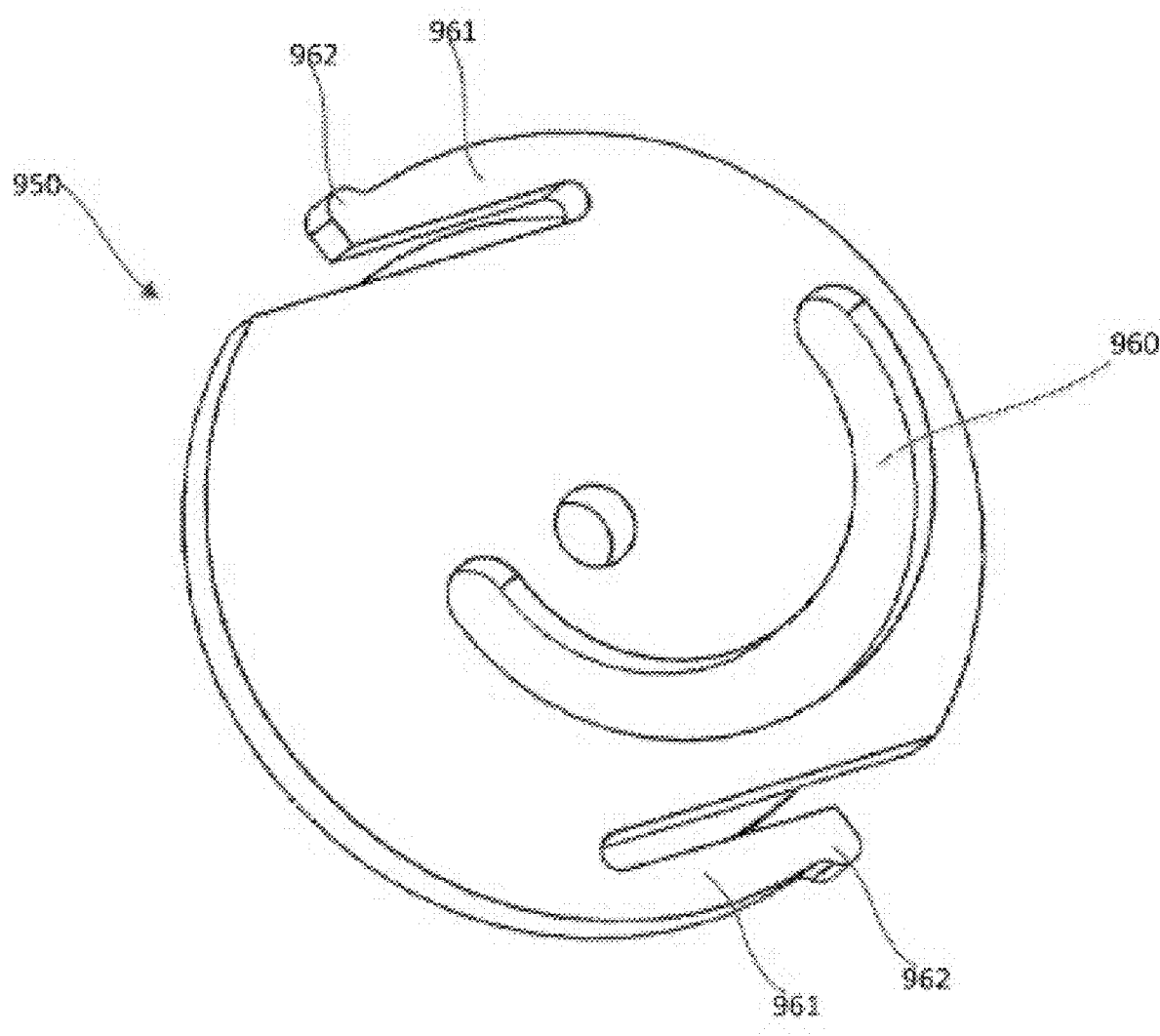
FIG. 10 depicts a bottom perspective view of a hub of the epicardial anchor of FIG. 3.
Figure 11:
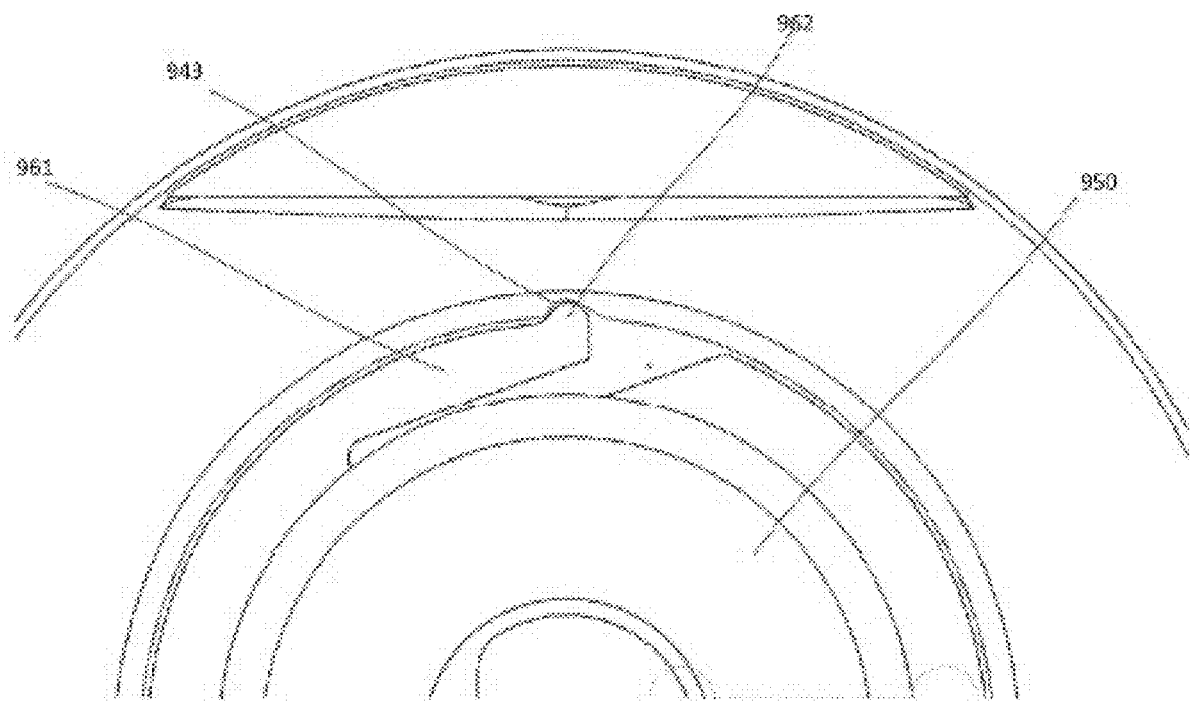
FIG. 11 depicts a top partial view of the epicardial anchor of FIG. 3.

An outer perimeter portion of the hub 950 is received within the retaining channel 951 such that the hub can rotate relative to the base member 940 to actuate the locking pin assembly 926 as described in more detail below. As shown, for example, in FIG. 9, the hub 950 includes arms 961 with protrusions 962. The protrusions 962 can be received within cutouts 943 of the base member 940 and act as a stop or limit to the rotation of the hub 950. The slots 963 defined by the hub 950 enable the arms 961 to flex and allow the protrusions 962 to be moved in and out of the cutouts 943. As shown, for example, in FIGS. 8 and 9, the hub 950 defines a curved channel 960 on a bottom portion of the hub. The curved channel 960 is asymmetrical (or spiral) and receives the driver portion 946 of the locking pin assembly 926. As the hub 950 is rotated relative to the base member 940, the hub acts as a cam to move the locking pin assembly 926 linearly within the locking pin channel 934. The locking pin assembly 926 can be moved from a first position in which the piercing portion 949 is disposed outside of the tether passageway 935 as shown in FIGS. 5 and 6, to a second position in which the piercing portion extends through the tether passageway 935. The pin member 953 (see, e.g., FIG. 7) can be formed with a metal material that is more radio-opaque than the other components of the anchor device and thus visible to the user (e.g. physician) using conventional imaging modalities to enable the user to confirm that the locking pin assembly 926 has been fully moved to the second position.

In use, when the locking pin assembly 926 is in the first position, a tether (not shown) coupled to, for example, a prosthetic mitral valve and extending through a puncture site in the ventricular wall of a heart can be inserted through the tether passageway 935. The hub 950 can then be rotated 180 degrees to move the locking pin assembly 926 linearly within the locking pin channel 934 such that the piercing portion 949 extends through the tether passageway 935 and engages or pierces the tether, securing the tether to the tether attachment member 924. For example, when the locking pin is in the first position, the protrusions 962 of the hub 950 are each disposed within one of the cutouts 943 of the base member 940 (i.e., a first protrusion is in a first cutout, and a second protrusion is in a second cutout). The hub 950 can then be rotated 180 degrees such that the protrusions 962 are moved out of the cutouts 943 of the base member 940 and at the end of the 180 degrees the protrusions are moved into the other of the cutouts of the base member (i.e., the first protrusion is now in the second cutout, the second protrusion is now in the first cutout).

Figure 12:
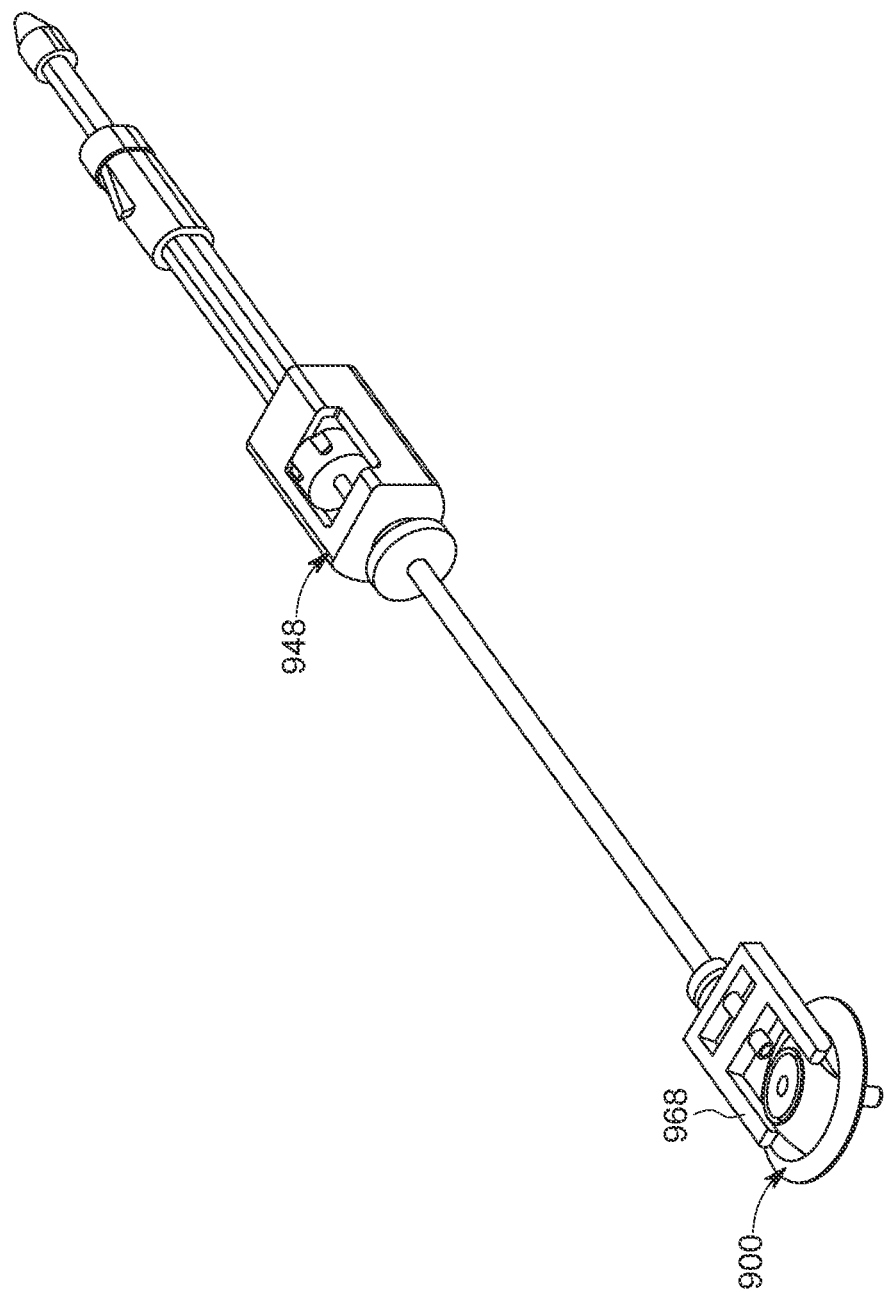
FIG. 12 depicts a perspective view of a delivery device engaged with the epicardial anchor of FIG. 3.

The base member 940 can also include cutout sections 966 and define side openings 967 (see, e.g., FIGS. 3 and 4) that can be used to couple a delivery device to the epicardial anchor device 900. For example, FIG. 12 illustrates a delivery device 948 having coupling arms 968 and coupling pins (not shown) extending inwardly from the arms 968. The side openings 967 can receive the coupling pins and the cutout sections 966 can be engaged by the coupling arms 968.

Figure 13:
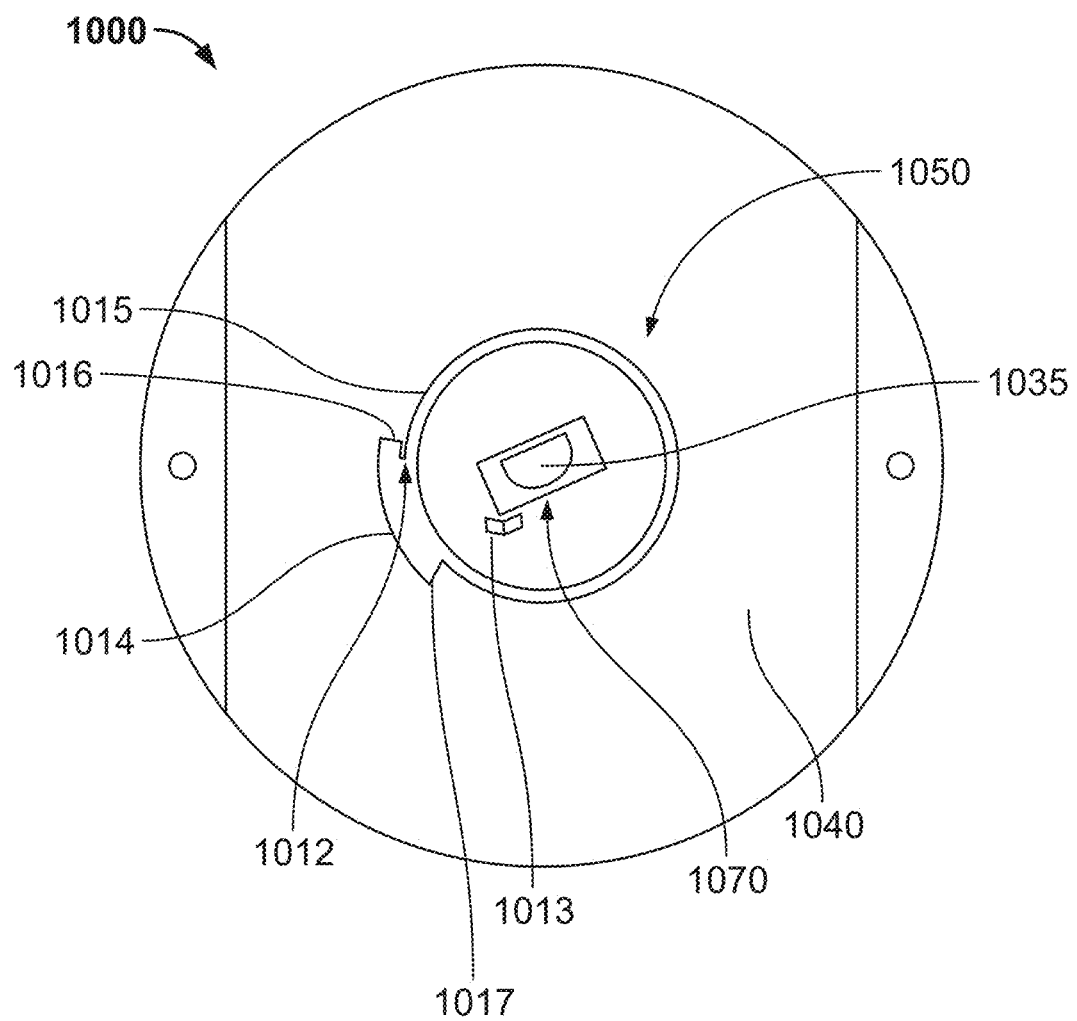
FIG. 13 depicts a top view of an epicardial anchor according to an embodiment of the present disclosure.

In another embodiment, FIGS. 13-17 depict an epicardial anchor device 1000, similar to that described above, having a base 1040 and a rotatable hub 1050. Hub 1050 includes a hinged tether capture device 1070 and an actuation mechanism 1013. Base 1040 is similar to base 940 as described above, and further defines a recessed portion 1014 and a rim 1015, the rim being generally circular and being interrupted by the recessed portion. Referring to FIG. 13, the view of anchor device 1000 shows the surface of the anchor device that faces away from the heart when the anchor device is in contact with the heart in the intended orientation. Generally, the tether of a prosthetic heart valve may pass through a tether passageway 1035 that extends through the base 1040 and the hub 1050. During the process of tensioning and securing the tether to the anchor device 1000, the tether may also pass through an opening in capture device 1070 while the capture device is in the orientation shown in FIGS. 13 and 15-16. The opening in capture device 1070 may be thought of as part of the tether passageway 1035. When the desired tension on the tether is achieved, the capture device 1070 may be actuated via actuation mechanism 1013 to capture the tether, with an excess length of the tether still protruding beyond the capture device 1070. Then, hub 1050 may be rotated to draw the excess length of the tether within an open volume bounded by the rim 1015 so that the excess length of tether is not freely floating within the anatomy. When actuated by actuation mechanism 1013, capture device 1070 rotates about its hinged connection to hub 1050 in a radial direction away from the longitudinal center of the anchor device 1000, so that a portion of the capture device is received within recess 1014. With the capture device 1070 partially received within recess 1014 and having captured a portion of the excess length of the tether, rotation of hub 1050 relative to anchor 1000 also rotates a portion of the capture device 1070, and the excess length of the tether, within an interior space of the anchor device 1000. The structures that provide for this functionality are described in greater detail below.

As shown in FIG. 13, hub 1050 is positioned at the longitudinal center of epicardial anchor device 1000. Hub 1050 lies on top of a hub portion of a tether attachment member (not shown), similar to hub 950 of tether attachment member 924 described above. Hub 1050 is freely rotatable with respect to the hub portion of the tether attachment member such that rotation of the hub 1050 does not affect the rotation of the hub portion of the tether attachment member. Hub 1050 is recessed within anchor 1000 that receives hub 1050 such that a top surface of hub 1050 is substantially flush with a top surface of base 1040. In alternative embodiments, the top surface of hub 1050 may be recessed below the top surface of base 1040. The portion of the tether passageway 1035 defined by capture device 1070 is aligned with the portions of the tether passageway defined by the base 1040 and the hub 1050 when the capture device 1070 is in the non-actuated state illustrated in FIG. 13.

Figure 14:
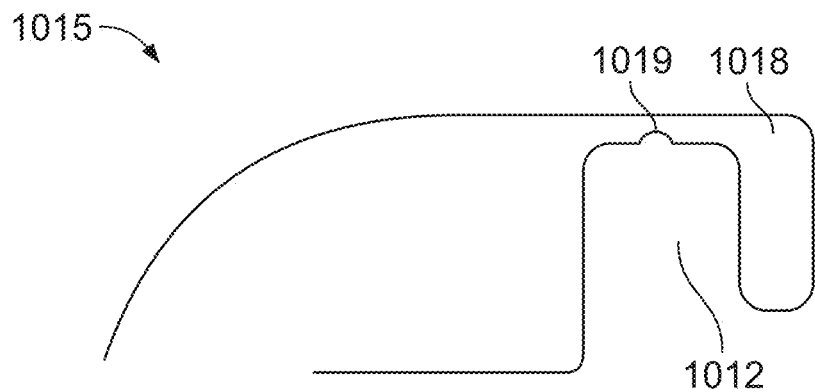
FIG. 14 depicts a cross-sectional view of a rim of the epicardial anchor of FIG. 13.

Referring now to FIGS. 13 and 14, the rim 1015 defined by the base 1040 circumscribes the hub 1050, with the exception of the interruption in the rim formed by the recess 1014. Hub 1050 is rotatably coupled to base 1040 such that the hub may be rotated relative to the base. This rotatable coupling may be achieved, for example, generally similar to that described above for the rotation of hub 950 relative to base 940. For instance, portions of hub 1050 may be at least partially contained within base 1040, such that rotational movement may be allowed while securing the hub from being axially displaced relative to the base. In an alternative aspect, base 1040 can be two components (not shown), a first top component and a second bottom component rotatably secured to the first component. In this manner, the second component of base 1040 can be rotated to actuate a locking pin assembly (not shown) similar to locking pin assembly 926, as described above, while hub 1050 and the first component of base 1040 remains stationary.

A cross-section of rim 1015 is illustrated in FIG. 14. Rim 1015 may be part of base 1040 and may be positioned along a substantially circular track on an interior perimeter of the base, adjacent an exterior perimeter of hub 1050, with the rim being interrupted by recess 1014. The rim 1015 may protrude radially inwardly from base 1040 a distance and have a rounded exterior surface along the outer circumference of the rim, however other shapes may be suitable, such as a chamfered surface, or the like. Recess 1014 may be spaced a distance radially away from the longitudinal center of hub 1050 greater than the distance at which the interior perimeter of the rim 1015 is spaced from the longitudinal center of the hub. The recess 1014 may be bounded by two opposing circumferential walls to allow for a portion of the capture device 1070 to be positioned between the opposing circumferential walls 1016, 1017 when the capture device is flipped via actuation mechanism 1013.

Still referring to FIG. 14, rim 1015 may include a lip or prong 1018 extending downwardly (toward the surface of anchor 1000 that is intended to contact the heart), the prong defining, in part, a track or void 1012 and at least one detent 1019. Void 1012 may extend in a circular direction to define a circular track that is interrupted by recess 1014. The tip of prong 1018 does not extend entirely to the surface on which hub 1050 is positioned so that the void 1012 is accessible through the space between the tip of the prong and the surface of base 1040 on which the hub is positioned. In alternative embodiments, there may be any number of detents 1019 along track 1012 of prong 1018.

Figure 17:
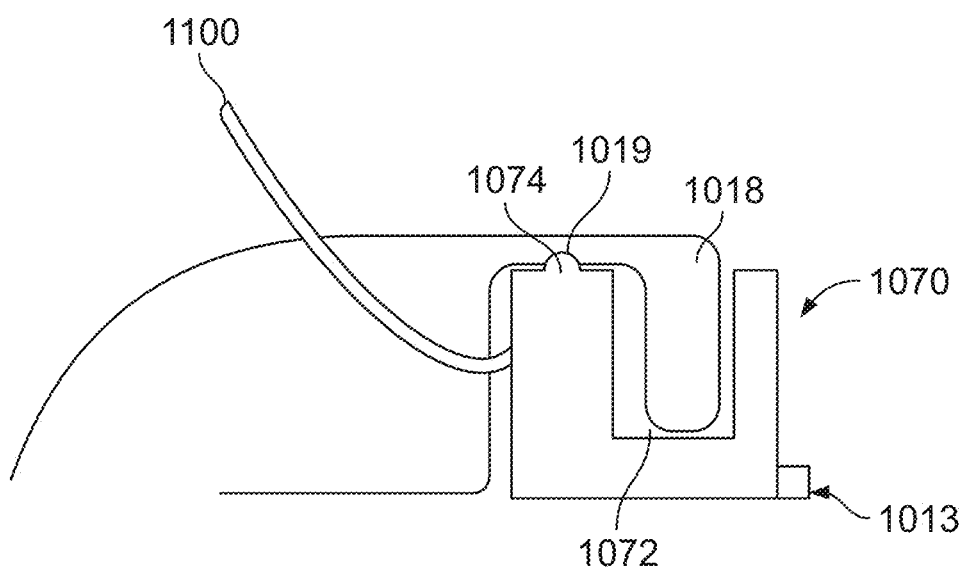
FIG. 17 depicts a cross-sectional view of the capture device received within the rim of epicardial anchor of FIG. 13.

With this configuration, when the capture device 1070 is flipped about the actuation mechanism 1013 (from the initial position shown in FIG. 15) so that a portion of the capture device is positioned within recess 1014, as illustrated in FIG. 17, the prong 1018 of rim 1015 may be received within cut-outs 1072 in the capture device and detent 1019 may receive a protrusion 1074 of the capture device. As is described in greater detail below, when the capture device 1070 receives a tether through tether passageway 1035, and the capture device is flipped via actuation mechanism 1013, a tether slot 1071 in the capture device captures the tether, and brings the captured portion of the tether into void 1012 as the capture device flips. After the capture device 1070 is flipped, and the hub 1050 is rotated, the capture device may also rotate, with the lip or prong 1018 helping to guide the rotation of the capture device, while the captured tether is drawn into the void 1012. In this manner, where the excess tether is looped multiple times within void 1012, the tether may stack on top of each itself, with both the stack of excess tether loops and body portion 1073 of capture device 1070 fitting within void 1012. Once a desired amount of excess tether has been looped within void 1012, hub 1050 may continue to be rotated until protrusion 1074 is received within detent 1019, providing a tactile feedback and locking force to the hub. It should be understood that although a protrusion 1074 is shown on capture device 1070, and one or more detents 1019 are shown in rim 1015, the rim may instead include one or more protrusions and the capture device may instead include a notch or detent to receive the one or more protrusions. Other temporary locking features, such as high friction contact portions, may be provided instead of the protrusion and detent configuration described above. In fact, any engagement system in which the capture device 1070 may be locked in a position relative to the rim 1015 may be suitable. Preferably, whatever engagement system is used, the capture device 1070 may be locked into the desired position, with an intentional rotational force on the hub 1050 being sufficient enough to move the capture device 1070 out of locking engagement with the rim 1015 to allow for the tether to be further wound (or to be unwound).

Figure 15:
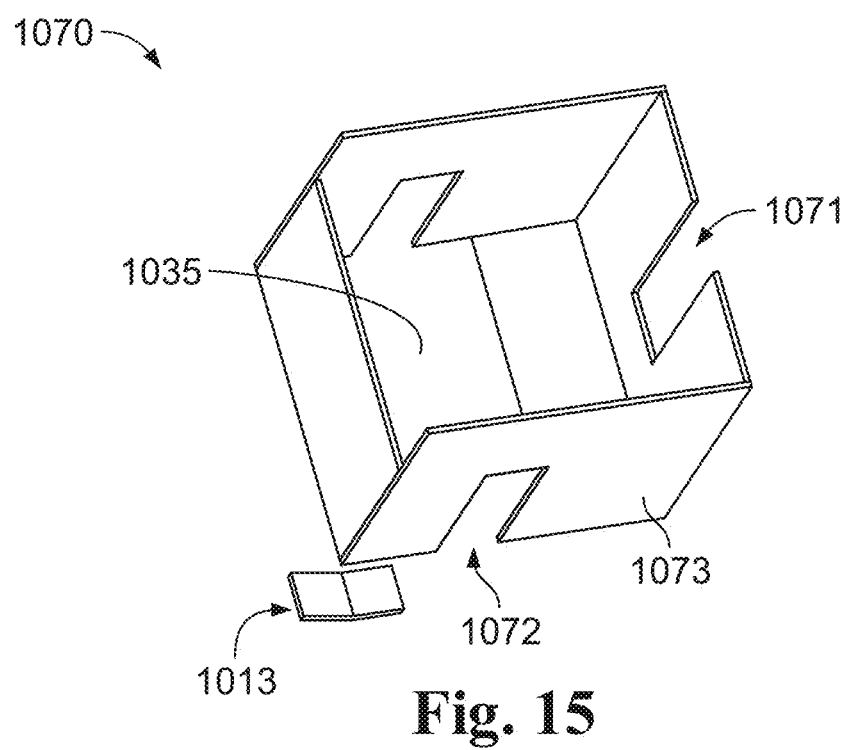
FIG. 15 depicts a perspective view of a capture device of the epicardial anchor of FIG. 13.

FIG. 15 depicts a perspective view of capture device 1070 and actuation mechanism 1013 prior to the actuation mechanism being actuated to flip the capture device 1070 into recess 1014. Capture device 1070 may have a predominantly rectangular or cube shape with actuation mechanism 1013 adjacent to a corner of capture device 1070, with the body portion 1073 and protrusion 1074 on the opposite side of the actuation mechanism. However, alternative embodiments of capture device 1070 may include one or more rounded corners to allow for capture device 1070 to be more easily flipped. In further alternative embodiments, there may be no protrusion 1074. Or, as noted above, the protrusion 1074 may be replaced with a notch, a high friction surface, or another component of a reversible locking engagement feature.

In a preferred embodiment, actuation mechanism 1013 is a button that, when pressed by the surgeon, flips capture device 1070 towards or away from recess 1014. This flipping may be performed through a spring (not shown) or other biasing mechanism attached to a portion of capture device 1070 such that actuation mechanism 1013 prevents capture device 1070 from moving until the actuation mechanism is pressed or otherwise actuated. Then, when actuation mechanism 1013 is pressed or otherwise actuated, the capture device 1070 is released so that the spring or other biasing mechanism flips the capture device 1070 so that a portion of the capture device is positioned within recess 1014. In use, capture device 1070 may be manually pushed back into its original position by the surgeon. This may be useful if the user needs to reverse the process of winding the tether, and it is desired to readjust the tension on the tether. Alternative actuation mechanisms may involve a lever system such that a surgeon pushing the lever in one direction pushes capture device 1070 in a direction toward/away from recess 1014 while pushing the lever in the opposite direction pushes the capture mechanism in the opposite direction. This lever system may be accomplished through a rod system where the lever is connected to a rod that runs through a portion of capture device 1070. A further alternative embodiment may involve the use of a wheel that uses a similar rod mechanism such that a surgeon may rotate the wheel one way or the other to flip capture device 1070. In yet another embodiment, a slider may be used with the rod system such that sliding the slider flips or unflips capture device 1070.

Figure 16:
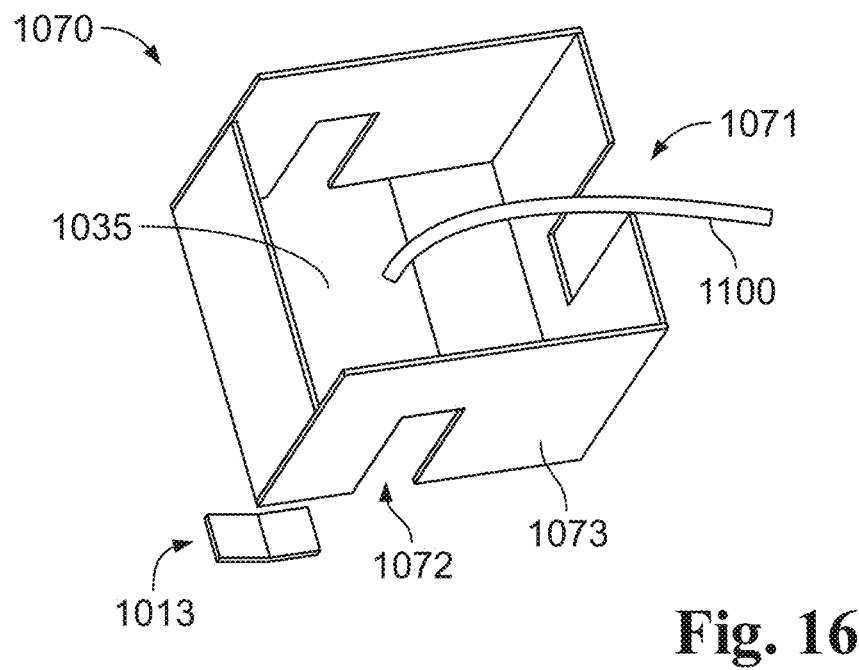
FIG. 16 depicts a perspective view of excess tether received in the capture device of FIG. 15.

FIGS. 16-17 depict a method of using anchor 1000 to wind an excess length of tether 1100 to store the excess length of the tether within the void 1012 of rim 1015. FIG. 16 depicts the capture device 1070 in a non-actuated condition, with an excess length of tether 1100 passing through passageway 1035. Prior to actuating the actuation mechanism 1013, the tether may be tensioned to the desired amount. When the tether is at the desired tension, it may be locked at that tension using a pin mechanism similar or identical to the locking pin assembly 926 described above.

When actuating actuation mechanism 1013, as the capture device 1070 begins to flip, the tether slot 1071 may tend to grab or capture the tether due to the relative positions of the tether slot and the tether. However, the surgeon may manually place the excess length of tether 1100 within the capture slot 1071 to help ensure the tether is appropriately captured when the capture device 1070 is flipped. Actuation mechanism 1013 may then be actuated by the surgeon, for example as described above, to flip the capture device 1070 into recess 1014, with the excess length of tether 1100 being drawn into the recess due to capture slot 1071 capturing and forcing a portion of the tether to move along with the capture device. With the capture device 1070 positioned at least partially within recess 1014, the surgeon may rotate hub 1050 in a clockwise or counter-clockwise direction such that body portion 1073 is received within void 1012 and prong 1018 is received within cut-outs 1072. As the hub 1050 is rotated and the capture device 1070 rotates with respect to rim 1015, the excess length of tether 1100 is drawn into the void 1012 causing the tether to wind within the base 1070. The hub 1050 may be rotated until excess tether 1100 has been sufficiently wound, at which point the surgeon may lock the hub 1050 to prevent the hub from being unintentionally rotated and the excess tether being inadvertently unwound.

Once a sufficient amount of excess tether 1100 has been wound within void 1012, hub 1050 may be further rotated so that protrusion 1074 is engaged with detent 1019. Such an engagement provides a tactile feedback and locking force to hub 1050 to prevent hub 1050 and excess tether 1100 from being unintentionally unwound from prong 1018. A plurality of detents 1019 may be provided at regular (or irregular) intervals along the circumference of the underside of rim 1015 such that multiple options are provided regarding where the capture device 1070 may reversibly lock to the rim 1015. Each time the protrusion 1074 encounters a corresponding detent 1019, the surgeon may receive feedback in the form of a tactile and/or audible "click." As noted above, alternative embodiments of securing hub 1050 to rim 1015 may include having the contact surfaces between body portion 1073 and the rim 1015 and/or prong 1018 be textured to provide a frictional force between the two contacting surfaces.

At this point, the prosthetic heart valve is in place and the tether is tensioned to the desired amount, with the excess length of the tether being wound within anchor device 1000 so that the excess length does not need to be physically cut away.

If it is desired to re-tension the tether, or even to remove the prosthetic heart valve, at any point prior to significant tissue in-growth occurring, the tether may be unwound so that the tether may be re-tensioned, or the anchor 1000 may be removed and the tether may be used as a rail to access the prosthetic heart valve to re-collapse the valve and remove it from the patient. To unwind the tether, the surgeon gains access to the anchor 1000 and rotates the hub 1050 in a direction opposite to the direction the surgeon rotated the hub when winding the tether. For instance, if the surgeon rotated hub 1050 in a counter-clockwise direction to wind the tether, the surgeon may rotate the hub in a clockwise direction to unwind the tether. The hub 1050 may be rotated with a sufficient force to overcome the reversible locking force between the engagement of protrusion 1074 and detent 1019 such that the protrusion disengages with detent 1019 and the capture device 1070 is again positioned within recess 1014. Once hub 1050 has been rotated to unwind the excess length of tether 1100, and the capture device 1070 is positioned within recess 1014, the surgeon may actuate actuation mechanism 1013 to flip the capture device 1070 back to its initial position, as shown in FIG. 16. In certain embodiments, instead of actuating the actuation mechanism 1013, the surgeon may manually flip the capture device 1070 back to its initial position. The surgeon may then re-tension the tether, or otherwise remove the anchor 1000 from the tether entirely and advance a separate device over the tether and into the heart in order to re-collapse the prosthetic heart valve into that device for explantation.

According to one aspect of the disclosure, an epicardial anchor system comprises:

a tether attachment member defining a portion of a tether passageway configured to receive a portion of a tether extending from a prosthetic heart valve;

a base having a rim defining a void along a circumference of the rim;

a tether capture device adjacent the tether attachment member and hingedly attached to the epicardial anchor, the tether capture device including an opening configured to receive the portion of the tether therethrough and a slot configured to capture the portion of the tether extending through the opening; and an actuation mechanism configured to flip the tether capture device from an unactuated condition to an actuated condition, wherein in the unactuated condition, the tether capture device is spaced from the void defined by the rim, and in the actuated condition, a first portion of the tether capture device is positioned within the void defined by the rim; and/or the tether capture device is positioned on top of the tether attachment member and/or the epicardial anchor includes a locking pin configured to secure the tether to the tether attachment member at a desired tension; and/or the base defines a recess along the circumference of the rim, the recess being sized and shaped to receive the first portion of the tether capture device following actuation of the actuation device; and/or the epicardial anchor has a top surface and the tether capture device has a top surface recessed with respect to the top surface of the epicardial anchor; and/or the actuation mechanism is adjacent a second portion of the tether capture device, the second portion being opposite the first portion; and/or the actuation mechanism is a button, a lever, or a wheel; and/or the rim further includes a prong and the tether capture device includes a cut-out, the cut-out being sized and shaped to receive the prong therein; and/or the rim has a detent and the first portion of the capture device has a protrusion configured to be received in the detent in a reversible locking engagement; and/or the detent includes a plurality of detents positioned at intervals around the circumference of the rim.

According to another aspect of the disclosure, a method of using an epicardial anchor comprising:

receiving a portion of a tether of a prosthetic heart valve within an opening of a tether capture device of the epicardial anchor while the prosthetic heart valve is positioned within a patient's heart;

actuating an actuation mechanism to flip the tether capture device so that a first portion of the tether capture device is received within a recess defined by a rim, the rim defined by a base of the epicardial anchor device, the recess interrupting a circumference of the rim; and capturing the portion of the tether in the recess upon actuation of the tether capture device; and/or the rim defines a void extending along the circumference of the rim, and the tether capture device is coupled to a hub of the epicardial anchor; and/or rotating the hub in a first direction to cause the tether capture device to travel circumferentially along the void, an excess length of the tether being wound into the void as the hub is rotated; and/or the rim defines a prong and the tether capture device defines a cut-out, the prong being received within the cut-out as the tether capture device travels circumferentially along the void; and/or rotating a hub in a second direction opposite the first direction after rotating the hub in the first direction, wherein rotating the hub in the second direction unwinds the excess length of the tether from the void; and/or locking the tether capture device in a desired position within the void to prevent unintentional movement of the tether capture device within the void; and/or locking the tether capture device includes engaging a protrusion of the tether capture device with a detent along the rim; and/or securing the tether to the epicardial anchor with a locking pin when the tether is at a desired tension; and/or the actuation mechanism is a button, a lever or a wheel.

According to another aspect of the disclosure, an epicardial anchor system comprising:

a tether configured to extend from a prosthetic heart valve;

a tether attachment member defining a portion of a tether passageway configured to receive a portion of the tether;

a base having a rim defining a void along a circumference of the rim;

a tether capture device adjacent the tether attachment member and hingedly attached to the epicardial anchor, the tether capture device including an opening configured to receive the portion of the tether therethrough and a slot configured to capture the portion of the tether extending through the opening; and an actuation mechanism configured to flip the tether capture device from an unactuated condition to an actuated condition, wherein in the unactuated condition, the tether capture device is spaced from the void defined by the rim, and in the actuated condition, a first portion of the tether capture device is positioned within the void defined by the rim.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of using an epicardial anchor comprising:

receiving a portion of a tether of a prosthetic heart valve within an opening of a tether capture device of the epicardial anchor while the prosthetic heart valve is positioned within a patient's heart;

actuating an actuation mechanism to flip the tether capture device so that a first portion of the tether capture device is received within a recess defined by a rim, the rim defined by a base of the epicardial anchor device, the recess interrupting a circumference of the rim, the rim defining a void extending along the circumference of the rim, and the tether capture device being coupled to a hub of the epicardial anchor;

capturing the portion of the tether in the recess upon actuation of the tether capture device; and rotating the hub in a first direction to cause the tether capture device to travel circumferentially along the void, an excess length of the tether being wound into the void as the hub is rotated.

2. The method of claim 1, wherein the rim defines a prong and the tether capture device defines a cut-out, the prong being received within the cut-out as the tether capture device travels circumferentially along the void.

3. The method of claim 1, further comprising rotating a hub in a second direction opposite the first direction after rotating the hub in the first direction, wherein rotating the hub in the second direction unwinds the excess length of the tether from the void.

4. The method of claim 1, further comprising locking the tether capture device in a desired position within the void to prevent unintentional movement of the tether capture device within the void.

5. The method of claim 4, wherein locking the tether capture device includes engaging a protrusion of the tether capture device with a detent along the rim.

6. The method of claim 1, further comprising securing the tether to the epicardial anchor with a locking pin when the tether is at a desired tension.

7. The method of claim 1, wherein the actuation mechanism is a button, a lever or a wheel.

\* \* \* \* \*